United States Patent [19]

Brown et al.

[11] Patent Number: 5,102,526

[45] Date of Patent: Apr. 7, 1992

[54] SOLID STATE ION SENSOR WITH SILICON MEMBRANE

[75] Inventors: Richard B. Brown; Geun-Sig Cha, both of Ann Arbor, Mich.

[73] Assignee: The University of Michigan, Ann Arbor, Mich.

[21] Appl. No.: 517,636

[22] Filed: May 2, 1990

[51] Int. Cl.⁵ .............................................. G01N 27/26
[52] U.S. Cl. .................................... 204/415; 204/418; 204/153.17
[58] Field of Search .................. 204/418, 403; 357/25; 435/288, 291, 180, 182

[56] References Cited

U.S. PATENT DOCUMENTS

| | | | |
|---|---|---|---|
| 4,236,987 | 12/1980 | Schindler et al. | 204/418 X |
| 4,269,682 | 5/1981 | Yano et al. | 357/25 |
| 4,305,802 | 12/1981 | Koshiishi | 204/418 |
| 4,388,165 | 6/1983 | Koshiishi et al. | 204/418 |
| 4,797,181 | 1/1989 | Durfor et al. | 204/418 X |
| 4,878,015 | 10/1989 | Schmidt | 204/418 X |
| 4,882,292 | 11/1989 | Sudhölter et al. | 357/25 X |

FOREIGN PATENT DOCUMENTS 43552 4/1981 Japan.

Primary Examiner—John Niebling
Assistant Examiner—Bruce F. Bell
Attorney, Agent, or Firm—Rohm & Monsanto

[57] ABSTRACT

A silicone matrix is employed to form a substance-sensitive membrane which is particularly suited for installation on a solid state sensor. The ionophore may be a potassium ionophore, an ammonium ionophore or any other ionophore. The membrane may be coupled to the molecule of interest through a bioactive agent, such as an enzyme, an immunochemical, bacteria, antibody, virus, or antigen. The resulting substance-sensitive membrane has electrochemical properties which compare favorably to those of conventional PVC membranes, and exhibit significantly greater adhesion to glasses and semiconductor substrate materials. The improved adhesion will prolong the life of the sensors and prevent the formation of electrolyte shunts which have been known to render solid state sensors inoperative.

13 Claims, 1 Drawing Sheet

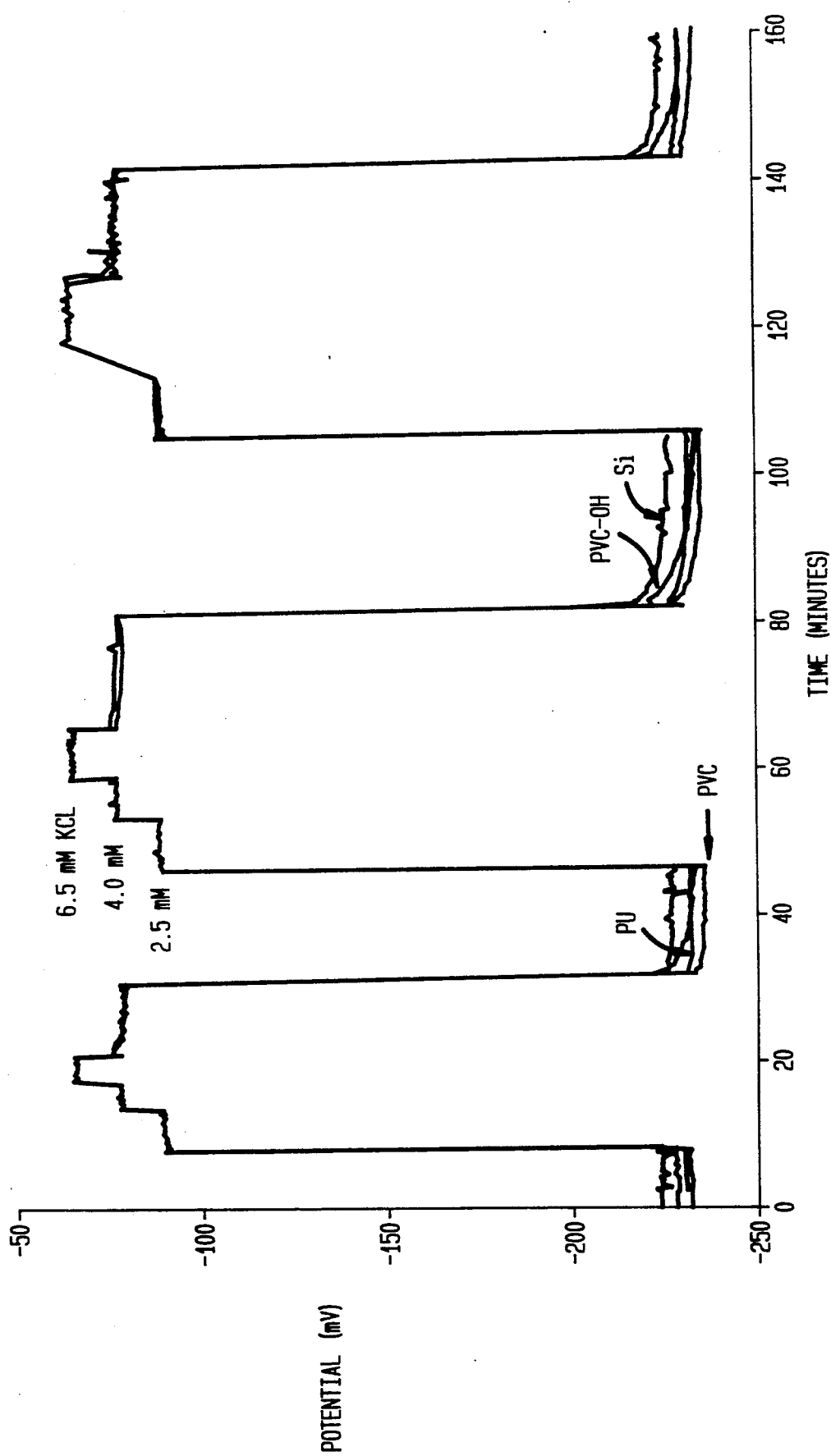

SOLID STATE ION SENSOR WITH SILICON MEMBRANE

BACKGROUND OF THE INVENTION

This invention relates generally to devices and systems for measuring concentrations of ions, chemicals, biological materials, and reaction products, and more particularly, to a solid state device which employs a silicone rubber matrix, having electrochemical properties comparable in quality to conventional PVC membranes, as the substance-sensitive membrane, and wherein the silicone rubber membrane exhibits excellent adhesion to the $Si_3N_4$ surface of solid state sensors.

As a result of their small size and potentially lower cost, solid state ion sensors are of interest in industrial and medical applications as replacements for traditional ion-selective electrodes. These sensors make possible new direct-monitoring applications. There is a need, however, for improved membrane adhesion, as such would be beneficial, not only to all users of solid-state chemical sensors, but particularly those interested in long-term monitoring.

Basically, the potential uses of solid-state ion sensors can be divided into industrial and medical applications. Industrial uses include, for example, the monitoring of treated or waste water for hardness or pollutants; on-line analysis of industrial chemicals, foodstuffs, and medicines; and low cost analytical instruments. Medical applications include the monitoring of electrolytes, blood gases, and metabolic substrates, both for biochemical control systems and for patient monitoring or diagnostics. There is a need for solid state ion sensors which can achieve the needs of industrial and medical monitoring for very long periods of time. Silicone-based chemical sensors often use ionophore-doped polymeric membranes as transducers because of their excellent selectivity toward the ion of interest, the wide range of ions for which ionophores are available, and because they can borrow from ongoing developments in ion-selective electrode technology. As is the case with ion-selective electrodes, most solid state sensors have used poly(vinylchloride) (PVC) as a membrane matrix. One of the primary causes of failure in conventional microsensors has been poor adhesion of the organic membrane to the chip surface. This leads to the formation of electrolyte shunts around the membrane, rendering the membrane inoperative.

Others in the prior art have endeavored to improve membrane adhesion such as by the use of a polyimide suspended mesh, modification of PVC for binding to hydroxyl-bearing surfaces, and mechanical attachment of the membrane. These methods have tended to improve adhesion of the membrane, but generally have resulted in either inferior electrochemical performance when compared to PVC or adding processing complexity. There is, therefore, a need for a permselective membrane which exhibits good electrochemical properties, preferably at least as good as traditional PVC membranes, but which exhibits excellent adhesion to the $Si_3N_4$ surface of solid state sensors.

Silicone has been used for forming chemical-selective membranes. Usually, such membranes are in the form of a silicone rubber tubing which is impregnated with an ionophore. In other known arrangements, the silicone rubber is pressed into a pellet. One commercially solvent castable two-part system which is based on silicone rubber has been employed to form chemical-selective membranes. However, the only success with this known approach has been in sensing pH. Moreover, the known approach produced a membrane which did not adhere well to surfaces.

It is, therefore, an object of this invention to provide a substance-sensitive solid state sensor which has an extended lifetime.

It is another object of this invention to provide a substance-sensitive membrane system for a solid state sensor which is possessed of excellent electrochemical properties.

It is also an object of this invention to provide a substance-sensitive membrane system for a solid state sensor which is characterized with excellent adherence to solid state sensor materials.

It is a further object of this invention to provide a substance-sensitive membrane system for a solid state sensor which can be applied to a plurality of solid state devices simultaneously using conventional integrated circuit manufacturing techniques.

It is additionally an object of this invention to provide a solid state sensor system which is not subject to the generation of disabling electrolyte shunts around the substance-sensitive membrane.

It is yet a further object of this invention to provide a solid state sensor system which is simple and low in cost.

It is also another object of this invention to provide a substance-sensitive polymeric membrane system for a solid state sensor which can be applied to a multiplicity of solid state devices simultaneously using conventional integrated circuit manufacturing techniques and which utilizes ionophoric doping to create the substance sensitivity.

It is yet an additional object of this invention to provide a substance-sensitive membrane for use with a solid state sensor and which does not require a structural layer associated therewith to maintain communication between the membrane and a solid state substrate.

It is still another object of this invention to provide a substance-sensitive solid state sensor which can be manufactured inexpensively in production quantities, and which can be adapted for industrial uses, such as monitoring treated or waste water for hardness or pollutants, on-line analysis of industrial chemicals, foodstuffs, and medicines, and low cost analytical instruments.

It is a yet further object of this invention to provide a substance-sensitive solid state sensor which can be manufactured inexpensively in production quantities, and which can be adapted for medical uses, such as monitoring of electrolytes, blood gases, and medical substrates.

It is also a further object of this invention to provide a substance-sensitive solid state sensor which can be manufactured inexpensively in production quantities, and which can be adapted for biochemical control systems.

It is additionally another object of this invention to provide a substance-sensitive solid state sensor which can be manufactured inexpensively in production quantities, and which can be adapted for patient monitoring and diagnostics.

A still further object of this invention is to provide a substance-sensitive membrane for use in a solid state sensor, wherein the membrane exhibits good adhesion to $SiO_2$ surfaces.

An additional object of this invention is to provide a substance-sensitive membrane for use in a solid state sensor, wherein the membrane exhibits good adhesion to Si$_3$N$_4$ surfaces.

Yet another object of this invention is to provide a substance-sensitive membrane for use in a solid state sensor, wherein the membrane exhibits a reduced electrical resistance characteristic and thereby yields reduced electrical noise for the sensor.

Another object of this invention is to provide a substance-sensitive membrane for use in a solid state sensor, wherein the membrane exhibits a reduced tendency to adsorb protein.

A yet further object of this invention is to provide a substance-sensitive membrane for use in a solid state sensor, wherein the membrane exhibits a reduced tendency to cause blood clotting.

SUMMARY OF THE INVENTION

The foregoing and other objects are achieved by this invention which provides an integrated circuit chemical sensor arrangement. The integrated circuit sensor is provided with an input electrode formed of a conductive material in the vicinity of a region formed of a silicon-based semiconductor material, and a permselective membrane having a predetermined electrochemical property and formed of a silicone-based compound. The silicon-based compound is arranged to be in adherence with the silicon-based semiconductor material, and in electrical communication with the input electrode. In this manner, a voltage responsive to the electrochemical property is produced at the input electrode.

In a preferred embodiment of the invention, the permselective membrane is formed of polydimethylsiloxane, which is commercially available (Petrarch-SS). A resistance-reducing additive, such as CN-derivatized silicone rubber is mixed into the polydimethylsiloxane, which serves to reduce electrical noise associated with a high impedance characteristic of the polydimethylsiloxane. In addition, an ionophore is mixed with the polydimethylsiloxane, which ionophore may be, for example, potassium or ammonium. In other embodiments, the sensors may be made responsive to other molecules through addition of bioactive agents, such as an enzyme, an immunochemical, a bacteria, and a virus.

In accordance with a process aspect of the invention, a substance-sensitive membrane is formed by the process of first mixing an ionophore into polydimethylsiloxane, and second mixing CN-derivatized silicone rubber into said dissolved polydimethylsiloxane.

In one embodiment of this process aspect of the invention, there is provided the further step of depositing the mixture of the polydimethylsiloxane, the ionophore, and the CN-derivatized silicone rubber onto a substrate. In other embodiments, the mixture may be solvent cast.

As previously noted, the ionophore may be, for example, an ammonium ionophore or a potassium ionophore. Illustratively, the ionophore is present in a proportion of 1 wt. % of the mixture. The CN-derivatized silicone rubber is present in the mixture in an amount of approximately 10 wt. %.

BRIEF DESCRIPTION OF THE DRAWING

Comprehension of the invention is facilitated by reading the following detailed description, in conjunction with the annexed drawing, which is a graphical representation illustrating the response of four different types of membranes to potassium, including a measurement in blood serum.

DETAILED DESCRIPTION

The present invention has been made by the inventors herein in the form of silicone-matrix membranes selective to potassium and ammonium. Such membranes exhibit good electrochemical properties and superb adhesion to silicon nitride. The highly beneficial adhesion characteristic was accomplished by using polydimethylsiloxane which advantageously is easily cured at room temperature by moisture activation. The polydimethylsiloxane (Petrarch-SS) is silanol-terminated and can be processed in the solvent tetrahydrofuran (THF). This silicone material exhibits extremely high bond strength to a wide range of substrates, including Si$_3$N$_4$. In addition, the polydimethylsiloxane exhibits reduced protein adsorption and blood clotting.

The foregoing notwithstanding, it is a problem with silicone membranes in general that they are characterized by high electrical resistance. This causes compromises in the electrochemical performance, illustratively in the form of signal noise. The signal noise associated with the high resistance characteristic can be improved by incorporating a plasticizer into the membrane, or one of the lipophilic additives, such as potassium tetrakis-parachlorophenyl borate, or cyano- group derivatized silicone rubber. Unfortunately, the use of a plasticizer causes poor adhesion. Of the other additives, CN-derivatized silicone rubber gives the best noise reduction. Accordingly, 10% by weight of this material is added to the polymer, along with 1% by weight ionophore.

The following table compares the electrochemical properties of four different membrane types toward potassium and ammonium. Although the silicone membrane appears to have a slightly inferior performance, its greatly superior adhesion characteristic will justify its use in many applications.

TABLE 1

| Composition of Matrix (wt %) | Slope (mV/decade) | | Detection Limit (μM) | | Selectivity $\text{Log}_{i,j}^{pol}$ | | | R | A |
|---|---|---|---|---|---|---|---|---|---|
| | | | | | i = K$^+$ | i = NH$_4^+$ | | | |
| | K$^+$ | NH$_4^+$ | K$^+$ | NH$_4^+$ | j = Na$^+$ | j = Na$^+$ | j = K$^+$ | | |
| PVC (33%) | 57.1 | 55.8 | 0.5 | 0.98 | −4.28 | −2.82 | −0.85 | 1.0 | P |
| PVC (20%) PVC/Ac/Al (20%) | 57.3 | 56.0 | 0.52 | 0.91 | −4.22 | −2.77 | −0.82 | 0.8 | G |
| PU (26.4%) PVC/Ac/Al (6.6%) | 57.2 | 56.8 | 0.59 | 0.99 | −4.21 | −2.89 | −0.89 | 0.9 | E |
| P-SS (78%) | 56.5 | 52.9 | 1.0 | 1.4 | −4.16 | −2.64 | −0.66 | 33.5 | S |

TABLE 1-continued

| Composition of Matrix (wt %) | Slope (mV/decade) | | Detection Limit (μM) | | Selectivity Log $K^{pot}_{i,j}$ | | | R | A |
|---|---|---|---|---|---|---|---|---|---|
| | | | | | i = K+ | i = NH4+ | | | |
| | K+ | NH4+ | K+ | NH4+ | j = Na+ | j = Na+ | j = K+ | | |
| Si—CN (21%) | | | | | | | | | |

PVC polyvinyl chloride
PVC/Ac/Al 80% vinyl chloride 5% vinyl alcetate 15% vinyl alcohol
PU polyurethane
P-SS polydimethylsiloxane
Si—CN 10-12% (cyanopropyl)methyl
R Normalized Resistance
A Qualitative Adhesion
P Poor
G Good
E Excellent
S Superb

[1]Potassium and ammonium selective membranes are doped with 1% valinomycin and nonactin, respectively. The balance of the menbrane is DOA (bis(2-ethylhexyl)adipato plasticizer. (The silicone rubber membrane contains no plasticizer.)

In the FIGURE, a graphical representation illustrates the response of the four different types of membranes to potassium, including a measurement in blood serum. It is evident from this FIGURE that the silicone membrane is eminently usable in a wide variety of monitoring situations.

Membrane adhesion is significant because it is one of the properties which determines the lifetime of solid state chemical sensors. In order to determine the adhesion characteristic during testing of the membranes of the present invention, and others, the well-known "Scotch tape test" was employed. The results of this testing process is shown below in tabular form in Table 2.

TABLE 2

ADHESION TESTS

| | Number of Membranes Removed | | |
|---|---|---|---|
| | Scotch-Tape Peel Test 30 Spots on Si3N4 | | Soak Test 24 Glass Tubes |
| Matrix Type | No SiCl4 | With SiCl4 | 6-hour Soak |
| PVC | 30 | 30 | 19 |
| PVC/(PVC/Ac/Al) | 30 | 30 | none |
| PU/(pvc/Ac/Al) | none | none | none |
| Silicone | none | — | none |

As set forth in Table 2, thirty membranes, each of four different matrices, were cast on silicon wafers upon which a Si3N4 film had been deposited. After the membranes were cured, the tape was pressed onto the membranes and then removed. None of the polyurethane or silicone rubber membranes came off, while all of the PVC and hydroxylated PVC membranes were removed.

In another experiment, wet adhesion was tested by coating glass tubes with each composition and soaking the tubes in water for six hours. When the tubes were rinsed with flowing water, many of the PVC coatings washed away from the glass tubes, but such was not the case for the polyurethane or silicone-based membranes.

In view of the fact that the foregoing tests are only semi-quantitative, a new adhesion test was designed. The membranes were cast on a Si3N4 surface of a wafer which had been scribed on the backside. The wafer was then cleaved, and mounted on a pull tester with one half attached to a load cell, and the other half to a stationary grip. The wafer halves were pulled apart, peeling the membrane from the surfaces, while the membrane peeling force was monitored by the load cell. With this test, the maximum pulling force required to peel each membrane from the Si3N4 surfaces was compared. These results are set forth below in Table 3.

TABLE 3

ADHESION TEST RESULTS

| | Normalized Pulling Force | | |
|---|---|---|---|
| | Dry | | Wet |
| Matrix Type | no SiCl4 | With SiCl4 | with SiCl4 |
| PVC | 1.00 | 1.49 | 1.01 |
| PVC/(PVC/Ac/Al) | 0.54 | 1.04 | 1.01 |
| PU/(PVC/Ac/Al) | 5.29 | 54.99 | 30.84 |
| Silicone | 57.87 | — | — |

As is evident from Table 3, the silicone rubber membrane had extremely strong bond strength. In fact, the bond strength of the silicone rubber membrane was so great that it exhibited cohesive failure rather than peeling. The membranes pulled apart at about 50 times the force required to peel the PVC membranes, but adhesive strength was higher than that since the membranes failed cohesively rather than adhesively. Thus, the adhesive strength of the membranes made in accordance with the present invention is greater than that shown in the table, and clearly greater than the adhesive strength of the other membranes. As expected, the adhesion of most of the membranes was decreased after soaking in water for 24 hours, but no change was seen with the silicone membrane.

There are many ways by which the membrane could be applied, including dipping, casting, spin-coating, screen printing, etc. Moreover, innumerable slight variations in the formulas could result in useful membranes. The simplest membranes are those containing ionophore to a specific ion. Such membranes should also be used in conjunction with, or incorporate in, the membrane matrix, a bioactive agent, such as an enzyme, an immunochemical, a bacteria, etc. Thus, the membranes can be made specific to more complex chemicals.

Although the invention has been described in terms of specific embodiments and applications, persons skilled in the art can, in light of this teaching, generate additional embodiments without exceeding the scope or departing from the spirit of the claimed invention. Accordingly, it is to be understood that the drawing and description in this disclosure are proffered to facilitate comprehension of the invention, and should not be construed to limit the scope thereof.

What is claimed is:

1. In an integrated circuit chemical sensor arrangement having an input electrode formed of a conductive material in the vicinity of a region formed of a silicon-based semiconductor material, a permselective membrane having a predetermined electrochemical property responsive to an ion through addition of an ionophore which is soluble in an organic solvent, and formed of a silicone-based compound arranged to be in adherence with said silicon-based semiconductor material and in electrical communication with said input electrode, for producing at said input electrode a voltage responsive to said electrochemical property.

2. The integrated circuit chemical sensor arrangement of claim 1 wherein said permselective membrane is further comprised of silanol-terminated polydimethylsiloxane.

3. The integrated circuit mechanical sensor arrangement of claim 1 wherein said permselective membrane is further comprised of a resistance-reducing additive.

4. The integrated circuit chemical sensor arrangement of claim 3 wherein said resistance-reducing additive is CN-derivatized silicone rubber.

5. The integrated circuit chemical sensor arrangement of claim 1 wherein said ionophore is a potassium ionophore.

6. The integrated circuit chemical sensor arrangement of claim 1 wherein said ionophore is an ammonium ionophore.

7. In a process for forming a substance-sensitive membrane for a solid state sensor arrangement, the process comprising the steps of:

first mixing an ionophore into polydimethylsiloxane; and second mixing CN-derivatized silicone rubber into said polydimethylsiloxane.

8. The process of claim 7 wherein there is provided the further step of forming a membrane by depositing said mixture of said polydimethylsiloxane, said ionophore, and said CN-derivatized silicone rubber mixed therein onto a substrate.

9. The process of claim 7 wherein there is provided the further step of casting said mixture of said polydimethylsiloxane, ionophore, and CN-derivatized silicone rubber.

10. The process of claim 7 wherein said ionophore in said step of first mixing is an ammonium ionophore.

11. The process of claim 7 wherein said ionophore in said step of first mixing is a potassium ionophore.

12. The process of claim 7 wherein said ionophore is present in a proportion of 1 wt. % of the mixture.

13. A process for forming a substance-sensitive membrane for a solid state sensor arrangement, the process comprising the steps of:

first mixing into polydimethylsiloxane an ionophore in an amount of approximately 1 wt. %; and second mixing CN-derivatized silicone rubber into said dissolved polydimethylsiloxane in an amount of approximately 10 wt. %.

* * * * *